United States Patent
Baratta

[11] Patent Number: 6,095,680
[45] Date of Patent: *Aug. 1, 2000

[54] NONDESTRUCTIVE FRAUDULENT FASTENER SCREENING AND COMPOSITION DETERMINATION DEVICE

[76] Inventor: Francis I. Baratta, 138 Ridge St., Arlington, Mass. 02174-1737

[*] Notice: This patent issued on a continued prosecution application filed under 37 CFR 1.53(d), and is subject to the twenty year patent term provisions of 35 U.S.C. 154(a)(2).

[21] Appl. No.: 08/850,986
[22] Filed: May 5, 1997
[51] Int. Cl.⁷ .................................................. G01N 25/00
[52] U.S. Cl. .................................................. 374/43; 374/12
[58] Field of Search .................................. 374/10, 12, 43, 374/44, 45, 130

[56] References Cited

U.S. PATENT DOCUMENTS

| | | | |
|---|---|---|---|
| 2,924,771 | 2/1960 | Greenberg et al. | 374/45 |
| 3,981,175 | 9/1976 | Hammond, III et al. | 374/10 |
| 4,255,962 | 3/1981 | Ashman | 374/10 |
| 4,381,154 | 4/1983 | Hammond, III | 374/43 |
| 4,385,843 | 5/1983 | Hammon, III . | |
| 5,052,819 | 10/1991 | Baratta | 374/43 |
| 5,667,300 | 9/1997 | Mandelis et al. | 374/43 |

Primary Examiner—William Oen
Attorney, Agent, or Firm—Jeffrey D. Marshall

[57] ABSTRACT

This invention presents an improved way to determine, nondestructively, the composition of an unknown material sample such as, for example, an alloy steel fastener or a carbon steel fastener of unknown standard grade. The procedure involves utilizing a pulse of heat from a focused laser or infrared heater to a spot at the end of a standard grade fastener of known length or applying a pulse of cold and then placing an infrared temperature detector a specific distance from the heat or cold source and measure the temperature-time transmission. Over an interval of time the nature of the transmitted pulse and the time variation of temperature causes a pattern that allows the determination of the alloy content of the bolt. The temperature-time signature of the bolt, the decay curve after shut-off and the slopes of the curves can be used to detect inferior or mismatched bolts in a laboratory, in a plant or production floor environment or in situ testing in installed equipment. The device will discriminate between the standard Society of Automotive Engineers designated standard grade 8 fastener and the grade 8.2 fastener and most of those used as counterfeits. In addition, it will distinguish between the grade 8 standard fastener, as well as the steel alloys accepted as substitutes for the grade 8 standard, and many of those carbon steel fasteners that are used as counterfeits and thus serve as a screening device in conjunction with established methods of determining the composition of metallic materials.

19 Claims, 9 Drawing Sheets

NONDESTRUCTIVE FRAUDULENT FASTENER SCREENING AND COMPOSITION DETERMINATION DEVICE

FIELD OF THE INVENTION

The present invention relates to the nondestructive determination of the composition of a material when comparing the heat transfer properties of a sample of the material with the heat transfer properties of a standard of a similar material, said standard or substitute having a desired composition.

The invention herein described has use for nondestructive qualitative determination of composition of a variety of materials and its use is discussed mostly with reference to counterfeit, mismarked, and substandard externally threaded carbon steel fasteners.

SUMMARY

The device will provide, broadly, a method of determining nondestructively the composition of an unknown grade of fastener by noting the thermal characteristics of the sample and matching or comparing said thermal characteristics with the thermal characteristics of a standard or equivalent fastener of the same general type material and of known composition. The method includes controllably applying a heat pulse or a cold pulse to the sample at a region to provide a time-varying temperature pattern in the sample, measuring the temperature of the same region thereof and comparing the time-varying temperature of pattern of the standard subjected to equivalent conditions for the same length of time.

This device will discriminate between the Society of Automotive Engineers, designated standard, SAE J 429, AUG83, grade 8 and lower grade 8.2 fasteners. In addition, it will distinguish between the grade 8 standard fastener and many of those carbon steel fasteners that are used as counterfeits. Also it will differentiate between the steel alloys accepted as substitutes for the grade 8 standard and the majority of counterfeit carbon steel fasteners. The device, in conjunction with established methods of determining the composition of metallic materials can be used as a mechanism to implement a screening method.

The objects of the present invention are to provide improvements over U.S. Pat. No. 5,052,819 for the nondestructive comparison of the composition of an unknown material sample to the composition of a known material sample and provide a mechanism for such a nondestructive comparison determination, and one that can be operated by persons with only a small amount of technical training.

Such improvements over the present state-of-the art consist of eliminating, in some instances, the need for an insulated environment and allowing in situ testing of those fasteners already assembled but accessible in components, as well as those whose ends are exposed to a medium, and the use of both noncontacting heating or application of a cold temperature and temperature sensing elements. Yet another improvement allows the ends of the fasteners to be exposed to a fluid. Further improvement is realized by examining: the slope of the temperature-time curves and the decay and slope of the temperature-time curves after the heat pulse is removed. Such improvements are applicable to field operations.

Still another object is to provide such a mechanism for the nondestructive determination of the composition of carbon steel and alloyed steel fasteners of known size (length and known weight).

Yet another object is to provide the foregoing mechanism for the nondestructive determination of the composition of carbon steel and alloyed steel samples in the form of fasteners and to give alarm in the event that a particular fastener fails to meet a standard.

The improved invention described herein allows for the temperature measurements at the ends at which the pulses of heat are applied to the standard and the sample. In this way, a comparison of temperature differences between the standard and fastener definitively reveals the temperature differences such that the Grade 8.2 or an acceptable substitute fastener can be sorted from the fraudulent Grade 8 or unacceptable fastener.

BRIEF DESCRIPTION OF THE DRAWINGS

Other and further objects advantages and features of the invention will be apparent to those skilled in the art from the following description thereof taken in connection with the accompanying drawings, in which.

BACKGROUND OF THE INVENTION AND PRIOR ART

Background

Figure 1:
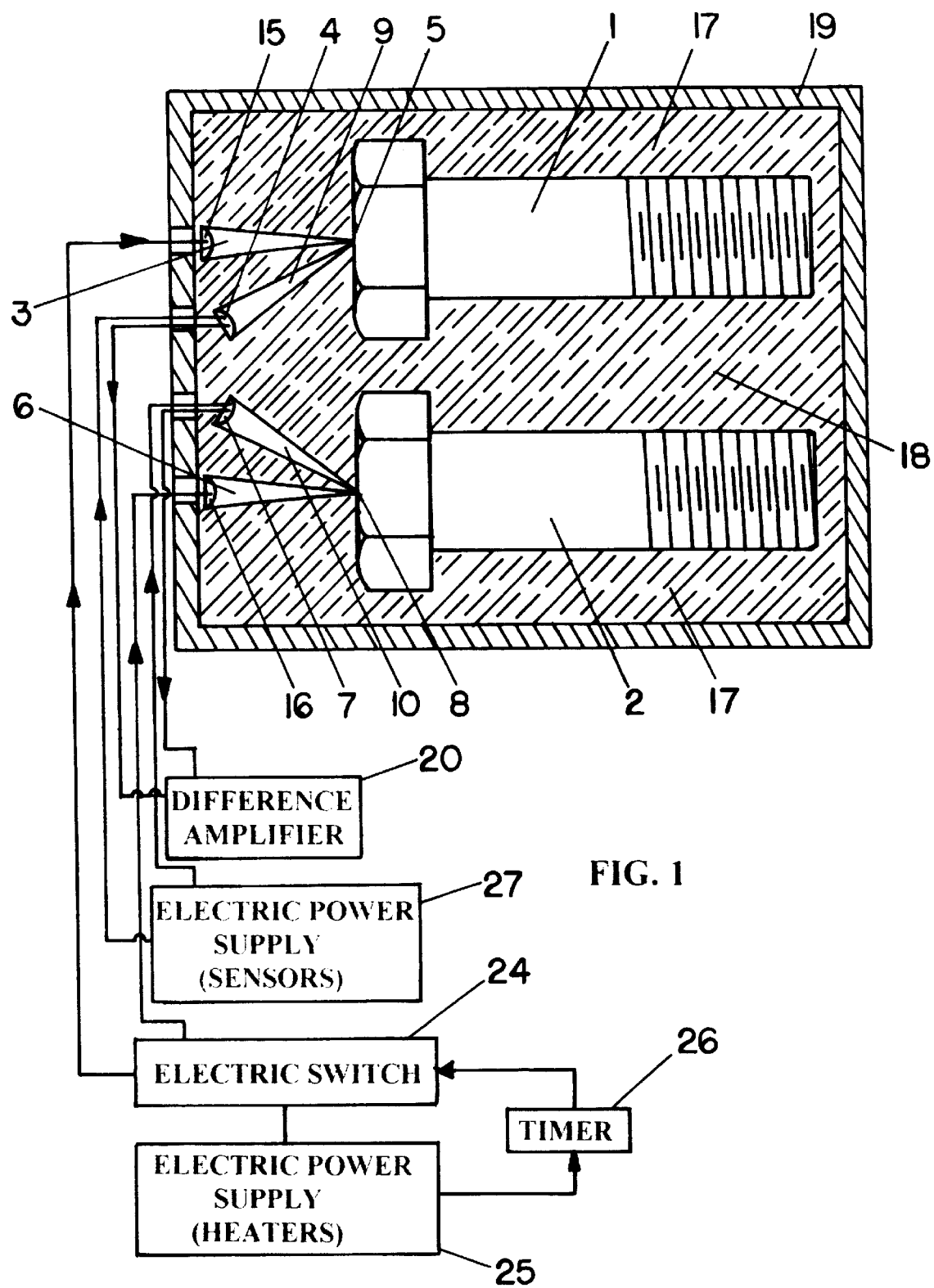
FIG. 1 is a diagrammatic representation, partly block diagram in form and the portions of the apparatus shown being partly cut away, of a system adapted to effect nondestructive determination of the composition of a material sample.

The recent influx of counterfeit threaded fasteners into the American economy has caused a multiplicity of problems, according to a report by the Subcommittee on Oversight and Investigations of the Committee on Energy and Commerce, U.S. House of Representatives. Unscrupulous manufacturers, importers and vendors have distributed and sold over thirty millions (as of 1988) of substandard fasteners in place of standard fasteners or acceptable substitute fasteners. The U.S. industries in the main utilize a standard for steel fasteners published by the Society of Automotive Engineers (SAE), SAE J 429 AUG83. (Although this specification refers to the SAE J 429 Standard and cites particular grades of fasteners as examples, equivalent acceptable grades of materials are used as substitutes.) As examples, lower grades 8.2 and 5.2 fasteners have been unknowingly bought by dealers and users in place of the higher grades 8 and 5 fasteners, respectively. Many of the lower grade fasteners have been falsely coded with the counterfeit grade identification markings.

It is noted that other steel alloys equivalent to SAE Grade 8 standard designated material have been used and accepted by the fastener industry as substitutes, such as: AISA 4140, AISA 41BV40, AISA 4141, AISA 41 BV41, etc.

Other carbon steels such as: AISA 1541, AISA 1020, AISA 1025, AISA 1027, AISA 1030 etc., have been used as counterfeit materials. Nevertheless, the discussions that follow for the sake of brevity will consider only SAE Grades 8 and 8.2, which will be sufficient to demonstrate the operating principle.

The major differences between the steel alloys designated as Grades 8 and 5; and the carbon steels designated as Grades 8.2 and 5.2 fasteners, specified by SAE J 429 AUG83, are in the percent permissible carbon and boron content, respectively. The Grades 8 and 5 contain higher amounts of carbon and therefore are of higher quality than Grades 8.2 and 5.2, respectively. Thus, additions of boron to Grades 8 and 5 steels, for the purpose of hardening, is unnecessary. The lower grade steel fasteners, Grade 8.2 and 5.2, have almost identical mechanical properties as the respective higher grade steel fasteners at ambient temperatures. However, following a high temperature excursion, the lower grade steel fasteners are susceptible to high temperature embrittlement, a condition that has led to catastrophic failures.

An additional difference between the Grade 8 and Grade 8.2 fastener is their heat treatments. Each however, will conform to the required minimum mechanical properties at room temperature but not at elevated temperature, because the Grade 8.2 fastener is of different composition and is tempered at a lower temperature than the Grade 8 fastener. Thus, grade 8.2 fasteners are subject to stress relaxation at somewhat lower temperatures then grade 8 fasteners. The surface hardness of each grade is almost identical and not amenable to detection by hardness testing. Thus, destructively testing by tensile tests above the tempering temperature of the Grade 8.2 and 5.2 fastener is required to definitively determine the grade of each fastener. Although both grades of fasteners are used at ambient temperature, the Grade 8.2 and 5.2 fastener will prematurely fail, compared to their respective higher grade fastener, due either to their greater susceptibility to stress corrosion cracking or hydrogen embrittlement.

The discussions that follow refer only to Grade 8 and Grade 8.2 fasteners, nevertheless, such comments are equally applicable to Grade 5 and Grade 5.2 fasteners. The discussions of the two types are essentially equivalent and would be needlessly repetitive. Also, the following discussion is generally applicable to the previously mentioned acceptable steel alloy substitute materials employed in the fastener industry and those fraudulent carbon steel fasteners manufactured and sold by illicit organizations.

Heretofore, the difference between the higher quality and lower quality fastener grades has been impossible to successfully detect in an accurate manner except by the costly destructive test method already mentioned and defined in SAE J 429 AUG83. Thus, it is important that some way be found to detect the bogus fasteners, a way that avoids the usual destructive testing, a way that is nondestructive, fast, simple and accurate. Such a detection method is needed that will stop the illegal sale of bogus fasteners and detect those already invoiced so that they can be sorted and separated from higher grade fasteners and allow each grade to be appropriately classified for future use.

Prior Art

Historically there are a number of methods used to determine the composition of metallic materials that have been classified as definitive and comparative: A method is considered definitive if it stands on its own, and to obtain results, does not require a sample with a known composition for comparison. It depends purely on chemical principles. Such methods are considered highly accurate and precise, but very tedious and slow to develop; sometimes taking days to provide answers. A comparative method is one, as the name implies, that requires a comparison to a known reference material. Such methods that have been developed and in use today are: optical emission spectrography, spectrometry, x-ray fluorescence spectrometry, atomic absorption spectrometry, plasma spectrometry and combustometric analysis to determine particular elements. These two general methods, definitive and comparative, require a sample from the test piece, that is in a sense they are destructive.

There are, however, several methods of nondestructively discriminating between bodies having similar appearances but of slightly different composition or even of different material. The following paragraphs discuss appropriate examples of these.

In one instance the relatively old technique of eddy current testing is utilized to attempt to separate higher grade fasteners from lower grade fasteners. This method principally compares the electrical conductivity, synonymous with thermal conductivity, and magnetic permeability of a resulting read-out wave form of the higher grade standard fastener to that of the sample.

According to SAE J 490 JUN84, the standard permissible variation in alloy content between Grade 8 and Grade 8.2 fasteners results in a very small percent difference by weight in the alloying elements. The minimum differences allowed in carbon (C) content by percent weight between Grade 8 and Grade 8.2 fasteners, dictated by SAE J 429 AUG83 are 0.27 C and 0.13 C, respectively. Such small differences in these major alloying elements that affect the conductivity and the permeability of the fasteners, result in an estimated difference (by a linear mixture approximation) in thermal conductivity between Grade 8 and Grade 8.2 fasteners of only 0.5%. This difference is very small and out of the sensitivity range of the eddy current technique.

In another instance U.S. Pat. No. 4,255,962, issued to Leland E. Ashman, teaches a method of distinguishing a simulated diamond from a natural diamond by utilizing a probe which applies a pulse of heat to the surface of the sample in an air environment and during the occurrence of thermal equilibrium the same probe detects the change in temperature. This change in temperature is related to the thermal conductivity of the sample. Since the thermal conductivity of natural diamond is at least an order of magnitude greater than a simulated diamond, such as cubic zirconia, it is readily detected. This method, however, is not sensitive enough to detect the slight change in thermal conductivity between Grade 8 and Grade 8.2 fasteners.

Another method of identifying materials nondestructively is disclosed in U.S. Pat. No. 2,924,771 issued to Elmer H.

Greenberg et al. This invention teaches an improvement in the employment of the thermoelectric effect to identify a specimen of material and in particular metallic materials. This method utilizes a pair of electrically connected metallic contact members engaged with a sample specimen, wherein one contact member, the probe, provides the hot junction and at a slightly different region the other contact provides the cold junction. Thus, a thermoelectric voltage reading is generated which is claimed to identify the material.

The disadvantages of the above mentioned test method are numerous, with the major ones listed by the following comments:

a. Reproducibility of the reading is dependent upon the relative thermal conductivity and thermal diffusivity of the probe and sample, as well as a properly proportioned probe geometry and contact area; and use of proper probe metal. In addition, resharpening of the probe with use is necessary.

b. Means have to be provided to minimize variable radiation losses in the contact members, otherwise the test becomes highly inaccurate. This necessitates calibration and control of additional heat to the system by the operator.

c. Optimum sensitivity is attained for different metals by previous tests of known specimens. Certain readings may be indicative of two or more metals. The ambiguity may be resolved by a single probe test wherein such results are then compared to a listing for that probe and may in all probability identify the specimen, if the diffusivities and thermoelectric effects are not too close.

d. Resulting test readings must be compared to a table of materials, each of known chemical analysis and physical condition when read with this method of standardization.

It is obvious from the noted disadvantages associated with the method described in U.S. Pat. No. 2,924,771, that it is not operator simple, reproducibility and accuracy is dependent upon a priori knowledge of the sample material, and results may well be ambiguous, such that the sample could not be definitively identified.

Another example of a nondestructive test method is described in U.S. Pat. No. 3,981,175, which was issued to Ogden H. Hammond III and Francis I. Baratta. In accordance with that system, the device is a nondestructive counterfeit gold bar detection system based upon heat transfer principles. The principle entails the application of identical finite suddenly applied controlled heat pulses at a first region which is one end of a gold bar of known purity, used as a standard, and the test bar of the same dimensions. The system is enclosed in an insulating medium. The temperatures, which are not only dependent upon the thermal properties of each bar, but upon the time are measured at a second region of each bar, located at the opposite ends of each bar. Specifically, those thermal properties which are tested by this devise are specific heat, thermal conductivity, and density; and the combination of these properties, known as thermal diffusivity. Since these properties of gold are unique, the temperature at the second region, specifically the end opposite from that which is suddenly pulsed by a quantity of heat, will be at a higher temperature in a given time than that of any bar less pure than the standard gold bar. Because of the large differences in thermal properties of gold and an alloyed gold sample, temperature measurements conducted at the far end will reveal differences. However, the thermal properties of the standard steel alloy fasteners, acceptable substitutes and the counterfeit carbon steel fasteners are very similar and temperature determinations at their far ends will not guarantee discrimination as will subsequently be shown.

Yet another example of a nondestructive test method to detect fraudulent precious metal bars is revealed in U.S. Pat. No. 4,381,154, issued to Ogden H. Hammond, III. It was found that of all possible forgeries, a non-alloyed tungsten forgery of gold, i.e., an insert of tungsten within the gold bar, is the most difficult to detect because the density and heat-capacity of tungsten and gold are virtually identical (a less difficult forgery to detect is an alloyed forgery wherein its composition is generally uniform throughout). Thus, an improvement in accuracy over the previous U.S. Pat. No. 3,981,175 was required. This improvement consists mainly of increasing the accuracy of the detection system by providing and controlling heat into the test chamber resulting in equilibrium, termed dynamic insulation; accurate heater control and using a compensated infrared sensor to measure the temperature at the far end opposite the heated end of the sample.

Although the improved techniques adopted in U.S. Pat. No. 4,381,154 will enhance the sensitivity of this test method it requires additional temperature sensors, controls and electronic instrumentation as compared to the method prescribed in U.S. Pat. No. 3,981,175.

The teaching of U.S. Pat. No. 3,981,175 and U.S. Pat. No. 4,381,154 applied a heat pulse at a first region and measured the temperature of the second region exclusively at the farthest end of the standard and sample, opposite of the first region. With a bar having the major composition of gold or other precious metals the heat transfer through the metal is excellent and the lengthwise travel of a thermal impulse to the one end can be determined. The addition of an adulterant are measurably affected by any deviation from the excellent thermal properties of gold and permit compositional discrimination of the alloy content at opposite ends of the bar, if the pulse length is appropriately chosen. This is readily shown by Table 1 below, where the temperature differences as a function of time are compared at the far end and at the near heated end of the gold bar and various adulterated bars 0.95 inches in diameter and 4.5 inches long.

TABLE 1

TEMPERATURE DIFFERENCES BETWEEN A PURE GOLD BAR AND ADULTERATED GOLD BARS OF 0.95 INCH DIAMETER AND 4.5 INCH IN LENGTH.

Heat input is 500 BTU/hr.
Temperature Difference in degrees F.

| Time | measured at far end | | | measured at heated end | | |
|---|---|---|---|---|---|---|
| | Mixtures | | | | | |
| sec | 5% Cu | 5% Ag | 5% W | 5% Cu | 5% Ag | 5% W |
| 0 | 0 | 0 | 0 | 0 | 0 | 0 |
| 5 | 0.01 | 0 | 0.02 | 2.14 | 0.96 | −0.51 |
| 10 | 0.29 | 0.03 | 0.13 | 3.03 | 1.36 | −0.71 |
| 15 | 0.88 | 0.09 | 0.30 | 3.71 | 1.67 | −0.86 |
| 20 | 1.62 | 0.20 | 0.47 | 4.31 | 1.93 | −0.97 |
| 25 | 2.39 | 0.34 | 0.62 | 4.88 | 2.17 | −1.06 |
| 30 | 3.16 | 0.49 | 0.74 | 5.45 | 2.38 | −1.11 |

These data were determined according to the governing heat transfer equations given in U.S. Patent Number 3,981,175. Note that when temperature differences are compared at the far end, positive differences are shown between the gold bar and all three alloyed bars examined. The bars examined consisted of 95% gold(Au) and 5% copper (Cu); 95% gold and 5% silver (Ag); and 95% gold and 5% tungsten (W). In these studies the temperature differences at the opposite ends of these bars, i.e., at the heated ends, show that the copper and silver alloys have positive differences, the other alloy, tungsten, shows a negative difference. This indicates that the method in U.S. Patent No. 3,981,175 will not always discriminate between a pure gold bar and an adulterated one when temperatures are measured at the heated ends of the bars. The teaching of this patent clearly indicates that transmission over the full rod length is needed to form complete discrimination of the gold alloy content.

A more recent U.S. Pat No. 5,052,819 was issued to Francis I. Baratta, which also taught a method of nondestructively identifying materials and fraudulent carbon steel fasteners. This invention, an improvement over U.S. Pat. No. 3,981,175, compares the characteristic temperature-time curve of a standard fastener to a test fastener by simultaneously providing a pulse of heat to both fasteners in an insulated receptacle and measuring the temperatures at their heated ends. The improvements are discussed in the paragraphs that follow.

In the case of materials such as alloy steels and carbon steels having less perfect thermal properties than those of precious metals, end to end thermal discrimination does not work. The failure of a lengthwise pulse is due to imperfect thermal properties as compared to pure gold and gold alloys. This is demonstrated by Table 2 below which again utilizes the governing heat transfer equations provided by U.S. Pat. No 3,981,175. Table 2 below, compares the temperature differences as a function of time at the far end and at the heated end of the fastener between a standard Grade 8 bolt with the maximum permissible percent chemical variation and a Grade 8.2 bolt with the minimum permissible percent chemical variation, as well as with a Grade 8 bolt with the minimum permissible percent chemical variation. (It is noted that the maximum permissible percent variation of chemical content for both the carbon steels and alloyed steels will result in a lower temperature during testing as compared to that of the minimum percent chemical variation.) These results show that discrimination is not feasible when the measurements are taken at the far ends of the fasteners. In this examined case, the comparison to the maximum percent chemical variation content grade 8 fastener to both the Grade 8.2 and the Grade 8 fastener with the minimum percent chemical variation content registers zero and a slightly positive temperature difference, respectively. These measurements show that the far end pulse detection is fatally flawed as a detection method to discriminate between the bolts. However, measurements at the heated ends of the fasteners show that a positive temperature difference is indicated only between the Grade 8 fastener of maximum permissible chemical variation content and the Grade 8.2 fastener of minimum permissible chemical content. This positive difference is sufficient to provide for a test that discriminates between these grades of bolts. Also, the negative difference between the grade 8 bolts of maximum percent chemical variation indicates that the test sample is also of grade 8 or equivalent.

Notice that the measured temperature differences at the heated ends shown in Table 2 are of magnitudes that are easy to detect even for the large fasteners used as examples. The heated ends of the fasteners are well below the heat treatment temperatures for the steels, so the test is truly a nondestructive test.

As mentioned above, U.S. Pat. No. 5,052,819 is an improvement over U.S. Pat. No. 3,981,175, which prescribed applying a heat pulse at the first end and measuring the temperature at the opposite end after a time interval. An example of this present improvement in testing by measuring the temperature near the input pulse is shown above that clearly indicates the superiority of this improvement as a test method. It is seen that a Grade 8.2 fastener will always be cooler at the prescribed temperature sensor location and prescribed time interval than the standard when each are subjected to the same conditions. Also if the test sample is of a higher grade it will test the same or higher than the standard data comparison and indicate a differential comparison of zero or less. However, U.S. Pat. No. 5,052,819 is quite restrictive in that it requires the standard fastener and the subject test fastener be completely insulated. Because there are millions of bogus bolts already emplaced in machine assemblies in the various industries throughout the united States and the world (see the report already cited by The Subcommittee on Oversight and Investigations) it would not be economically feasible to disassemble all of these components for testing. Further, the method of applying the heat pulse requires good thermal contact between the fasteners and the heating elements as well as the temperature sensing devices. This also requires that the threaded ends of the fasteners be finished machined with a spherical radius and a spring force be incorporated in the system to insure the necessary good contact.

Because the thermal properties of ferrous materials are not as unique as gold or silver, innovative improvements of U.S. Pat. No. 3,981,175 as well as overcoming the cumbersomeness of U.S. Pat. No. 5,052,819 are required to nondestructively detect counterfeit, mismarked, and substandard steel fasteners in a viable manner.

TABLE 2

TEMPERATURE DIFFERENCES BETWEEN STANDARD SAE J 429 AUG83 GRADE 8 MAXIMUM PERCENT CHEMICAL VARIATION CONTENT COMPARED TO MINIMUM PERCENT CHEMICAL VARIATION CONTENT FOR GRADES 8.2 AND GRADE 8 BOLTS; DIAMETER 1 INCH AND LENGTH 1 FOOT, MEASURED AT THE FAR END AND THE HEATED END.

| | Heat input in chart is 500 BTU/hr Temperature Difference in Degrees F. | | | |
|---|---|---|---|---|
| | Measured at far end | | Measured at heated end | |
| Time | % Minimum Permissible Chemical Variation | | | |
| sec | 8.2 bolt | 8 bolt | 8.2 bolt | 8 bolt |
| 0 | 0 | 0 | 0 | 0 |
| 5 | 0 | 0.01 | 0.05 | −0.08 |
| 10 | 0 | 0.02 | 0.07 | −0.10 |
| 15 | 0 | 0.03 | 0.09 | −0.12 |
| 20 | 0 | 0.04 | 0.10 | −0.13 |
| 25 | 0 | 0.06 | 0.12 | −0.14 |
| 30 | 0 | 0.07 | 0.13 | −0.15 |

DESCRIPTION OF THE PREFERRED EMBODIMENTS

In the description of the preferred embodiments that now follows, the invention is first discussed with reference to a system for determining nondestructively the composition of an unknown sample in rod form and, to simplify the explanation, the samples taken up are alloy steels and carbon steel fasteners, but it will be kept in mind that most aspects of the system discussed with respect to such fasteners may also apply to other materials not having unique thermal properties as those of gold.

It is noted that in the descriptions that follow where reference is made to the application of discontinuance of heat to the various bodies, it is understood to be equally applicable to cryogenic applications as well, although this is not stated in each case for the sake of brevity.

Turning now to FIG. 1, the apparatus shown is an improvement over that given in U.S. Pat. No. 5,052,819 and is for such nondestructive determination, a solid elongate sample or fastener I of unknown precise composition which is compared with a solid elongate standard or fastener 2 of known composition, as now explained. Rather than utilize contacting electric resistance heaters and contacting temperature sensors, the first embodiment and improvement consists of a laser or infrared heater 3, which applies focused heat via a lens 15 to the sample 1 at an end 5 thereof and, at the same time, an identical laser or infrared heater 6 applies focused heat via a lens 16 to the standard 2 at an end 8 thereof, thereby to provide time-varying temperature patterns in the sample and the standard. Simultaneously, with or at a predetermined time after the heat is applied and for a predetermined time interval, or after the heat has been shut off and for a predetermined time interval, the temperatures or time-varying temperature patterns of the sample, and the standard are sensed or noted and compared. The sensing functions are provided by an infrared sensor 9 focused by a focal lens 4 on sample 1 at its end 5 and an identical infrared sensor 10, focused by a focal lens 7 on the standard 2 at its end 8 operatively disposed to sense the time varying temperatures at ends 5 and 8, respectively of the sample and the standard, thus providing as output an electrical signal that is a function of the time-varying temperature. Each pair of heater means and temperature sensor means are well insulated from each other. The two electrical signals are connected as inputs to a difference amplifier 20 which notes any difference between the two electrical signals due to a temperature differential and amplifies the same.

Figure 2:
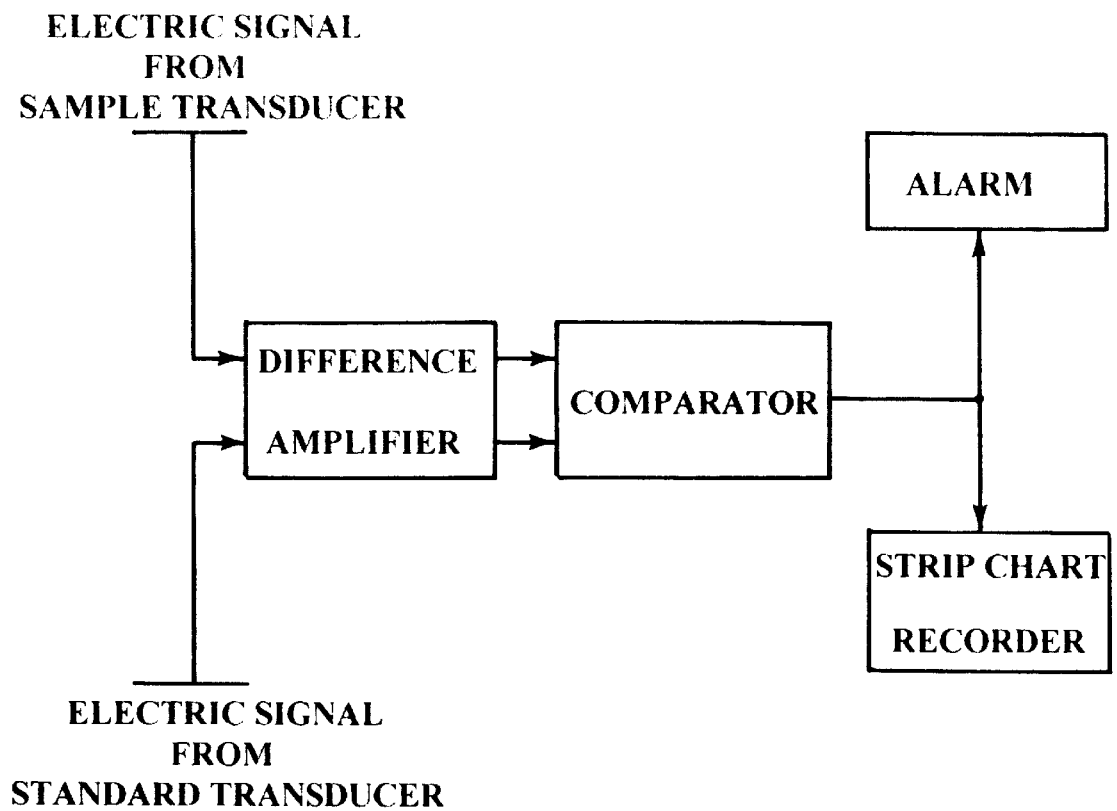
FIG. 2 shows in block diagram form a part of the system of FIG. 1, but slightly modified.

In FIG. 2, a comparator is connected to receive an output from the difference amplifier and is connected to an alarm which is activated in those instances in which the alloying content of sample 1 varies from that of the standard 2, or to a recorder or similar device. To complete the electric circuitry of FIG. 1 by which sample composition is evaluated or analyzed, the heaters 3 and 6 are electrically energized through a switch 24 from an electrical power source 25. The sequencing and timing of the events in the system is provided by a timer means 26.

In the apparatus shown by FIG. 1, the heating element 3 and temperature sensor 9, heating element 6 and the temperature sensor 10 are focused on one end of the unknown fastener sample and the standard fastener, respectively, as noted above. Although the bolt head end of the fastener is shown as being instrumented, the threaded end of the bolt could also have been chosen as the instrumented point. The length of each fastener must be known. This can be readily accomplished through exterior means by physical measurement or, for example, done through additional instrumentation and sensors built into the testing apparatus (this is not shown in FIG. 1 so as to retain clarity). At the heated ends of the fasteners are focused infrared sensors 9 and 10 powered, if required, by an electrical power source 27, to determine the temperature at said location of each fastener and, most important, to determine the relative changes in temperature in some time pattern which will give rise to a temperature difference.

For the best efficiency the fasteners, heaters, and temperature sensing devices should be well insulated from the environment. Note that unlike U.S. Pat. No. 5,052,819, mechanical means to provide good thermal contact and end machining of the fasteners were essential, but unnecessary here. Each fastener, heating element, and temperature sensor should be well insulated from each other and the other fastener, heating element, and temperature sensor. (In FIG. 1 the fasteners 1 and 2 are separated from one another, and thermal insulating material 17 and 18 is placed around and between the fasteners. In the actual apparatus the housing labeled 19 within which the fasteners are placed has an insulating recess to receive each fastener). Each heater means 3 and 6 should be of a type that provides controlled heat input as opposed to a lo constant temperature source; the heat thus applied is a controlled amount and the heating elements 3 and 6, by their physical nature, have low heat capacity so that all of the heat generated therein is transferred to the associated fasteners 1 and 2. It is noted that in U.S. Pat. No. 5,052,819 a precautionary statement was made which required that heating elements be of low heat capacity. Low heat capacity heaters are found to be best; they provide a concentrated amount of heat in a small area. If heat (e.g., a square wave pulse of indefinite duration) is applied to one end of a fastener at x=L, the general equation, which applies to the first embodiment represented by FIG. 1, for the temperature at any distance x is given by the expression:

$$T(x, t) = QL/k \left\{ \alpha t / L^2 + (3x^2 - L^2)/6L^2 - \right.$$

$$\left. 2/\pi^2 \sum_{m=1}^{\infty} (-1)^m / m^2 [\exp(-\alpha m^2 \pi^2 t / L^2)] \cos(m\pi x / L) \right\}$$ (1)

where: Q is the suddenly applied constant heat flux applied over a unit area (BTU/sec-ft$^2$) at x=L, L is length in feet, k is the thermal conductivity (BTU/sec-ft- F), $\alpha = k/\rho c$, and is the thermal diffusivity in ft$^2$/sec, c is the specific heat (BTU/lb-F), $\rho$ is the density in lbs/ft$^3$, t is time in seconds, x is the distance in feet along the bar and T(x,t) is temperature in degrees F. Note at x=0, at the far end of the bar, there is no flow of heat because of the insulation of the bar. (See Carslaw and Jaeger "*conduction Heat in Solids,*" Oxford Press, 1950, page 104, paragraph 43, eq. (1).)

If the temperature is measured at x=L, at the same end at which heat is applied, equation 1 becomes:

$$T(t) = Q \left\{ t / \rho c L + L/3k - \right.$$

$$\left. 2L/k\pi^2 \sum_{m=1}^{\infty} (-1)^m / m^2 [\exp(-\alpha m^2 \pi^2 t / L^2)] \cos(m\pi) \right\}$$ (1A)

If an attempt is made to counterfeit a fastener, the weight W in pounds and the length L in feet, would be dependent upon its size. Thus, equation (1A) becomes:

$$T(t) = q/W \left\{ t/c + L^2 \rho / 3k - \right.$$

$$\left. 2L^2 \rho / \pi^2 k \sum_{m=1}^{\infty} (-1)^m / m^2 [\exp(-\alpha m^2 \pi^2 t / L^2)] \cos(m\pi) \right\}$$ (1B)

Where: q is the suddenly applied constant heat flux in BTU/sec and all other terms are as defined above.

It is sufficient that at all times during the test interval, the temperature at the heated end of the suspected counterfeit fastener be as high as that of the known fastener (or a recording thereof). If the fastener in question has the same alloying elements and within the prescribed minimum and maximum percent chemical variation limits as the higher grade fastener, as given in SAE J 429 AUG83 and SAE J 490 JUN84, or an acceptable substitute, then it will be as hot or hotter as the higher grade fastener used as a standard for comparison. (Note, for example, that the maximum percent chemical limit of alloying elements resulting in the minimum percent of iron are used as the higher Grade 8 standard for comparison and thus the fastener in question, if it is Grade 8.2, will be lower in temperature than the standard for comparison). This is subject to several restrictions and possible errors which are taken up in the next paragraph.

Figure 3:
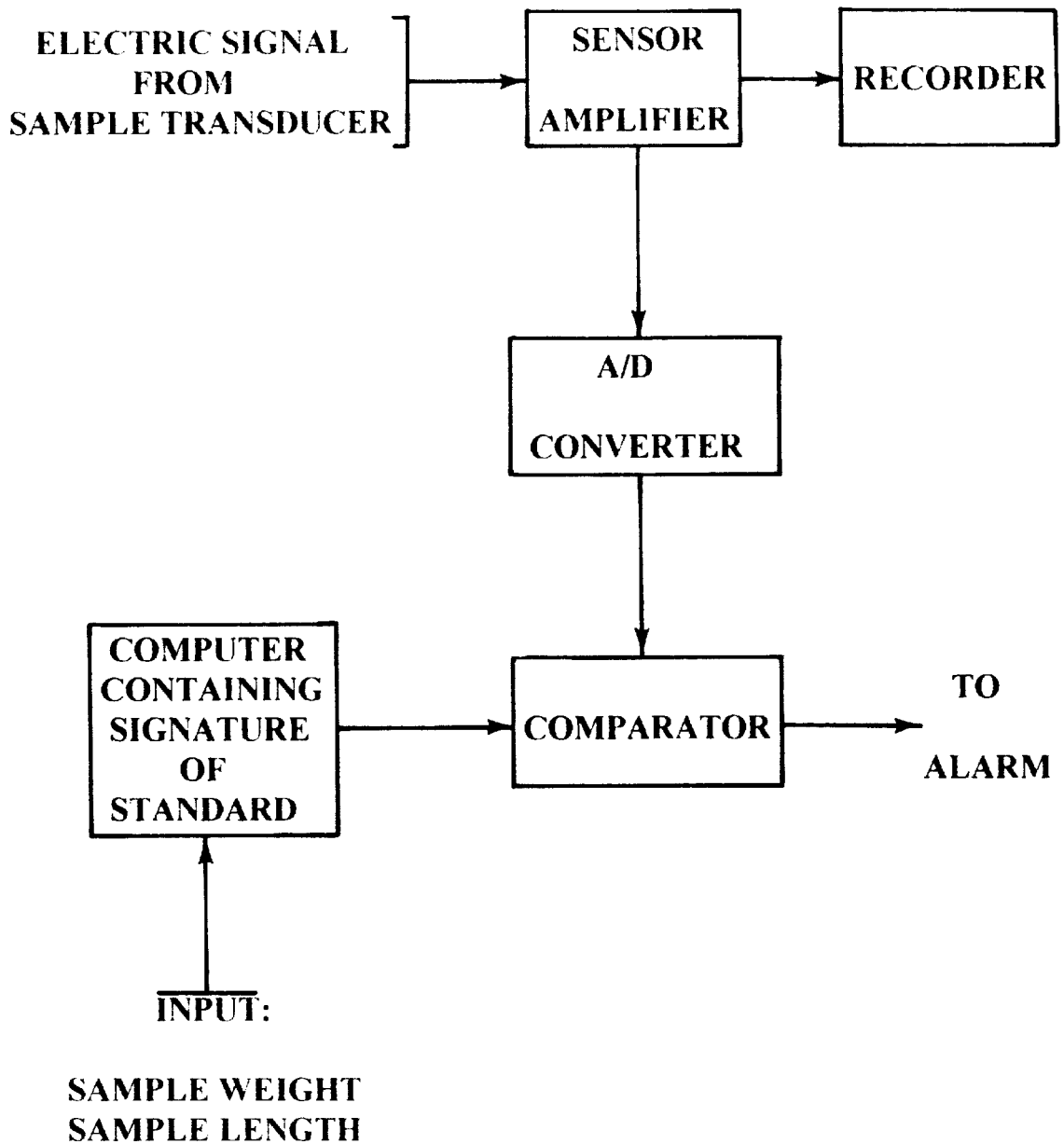
FIG. 3 shows in block diagram form another modified version of a part of the system of FIG. 1.

If the beam sizes of the heating elements 3 and 6, as shown in FIG. 1, are similar in size to the cross sectional area of the fastener, then equation 1B applies. Use of this equation, which was also employed to generate the data of Table 2, requires that the ratio $q_{sa}/W_{sa}=q_{st}/W_{st}$ (wherein $q_{sa}$ and $q_{st}$ are the heat inputs to the sample and standard of respective weights $W_{sa}$ and $W_{st}$) must be kept within acceptable tolerance. The test is as good as the exactitude with which the lengths and weights are known. It may be impracticable to match lengths and weights of the test sample fastener and the standard fastener for comparison. However, it is not necessary that the standard actually be present at the time the sample is tested. Thus, in FIG. 3 the time-varying patterns of a sample fastener, converted to electric signals as before, are fed to a sensor amplifier and thence to an analog-to-digital converter, the output of the converter being connected as one input to a comparator, the other input, which is from a computer, allows the measured length and weight of the sample fastener, and has stored the signatures of an equivalent standard. Note the measurement of length and weight can be integral to the test device (for simplicity this is not shown in FIG. 1) and automatically programmed into the computer as shown in FIG. 3, or be manually programmed. The output of the comparator can connect to an alarm. Also, the sensor output can be connected as outputs to a recorder.

A second embodiment and another improvement is realized when a noncontacting heat pulse such as a lasers or infrared heat source 3 and 6 are utilized, as shown in FIG. 1, and concentrated on small areas 5 and 8 respectfully, then only the lengths of the standard and test sample are needed and their weights need not be known. The length of the test sample can be predetermined by physical measurement or supplementary instrumentation and sensors can be built into the system. This is neither shown nor discussed because it is not necessary to the understanding of the proposed concepts. For such a case equation (1A) is applicable. It is important to know the area of the focused spot of heat since the heat pulse is defined as the suddenly applied heat flux expressed per unit area. Also, both sensors are located within three to four diameters distant in relation to the diameter of the areas of their respective heaters.

The third embodiment can be realized by determining the slope and shape of the temperature-time curve and this is readily obtained by taking the first derivative of equation (1) and is:

$$dT/dt = Q/\rho cL\left\{1 + 2\sum_{m=1}^{\infty}(-1)^m \exp(-\alpha m^2\pi^2/L^2 t)\cos(m\pi x/L)\right\} \quad (2)$$

At the heated end where x=L, equation (2) becomes:

$$dT/dt = Q/\rho cL\left\{1 + 2\sum_{m=1}^{\infty}(-1)^m \exp(-\alpha m^2\pi^2/L^2 t)\cos(m\pi)\right\} \quad (2A)$$

And at the far end where x=0, equation (2) becomes:

$$dT/dt = Q/\rho cL\left\{1 + 2\sum_{m=1}^{\infty}(-1)^m \exp(-\alpha m^2\pi^2/L^2 t)\right\} \quad (2B)$$

Similarly, slope equations such as those given by equations (2A and (2B) can be obtained by differentiating equation (1B), which are:

$$\text{At } x = L: \quad (3)$$

$$dT/dt = q/Wc\left\{1 + 2\sum_{m=1}^{\infty}(-1)^m \exp(-\alpha m^2\pi^2/L^2 t)\cos(m\pi)\right\},$$

$$\text{And at } X = 0: \quad (3A)$$

$$dT/dt = q/Wc\left\{1 + 2\sum_{m=1}^{\infty}(-1)^m \exp(-\alpha m^2\pi^2/L^2 t)\right\}$$

Appropriate instrumentation associated with the application of equations (2A), (2B), (3) and (3A) can be readily employed. However, the description of such instrumentation is not given because it is not necessary to the understanding of the concept.

Figure 4:
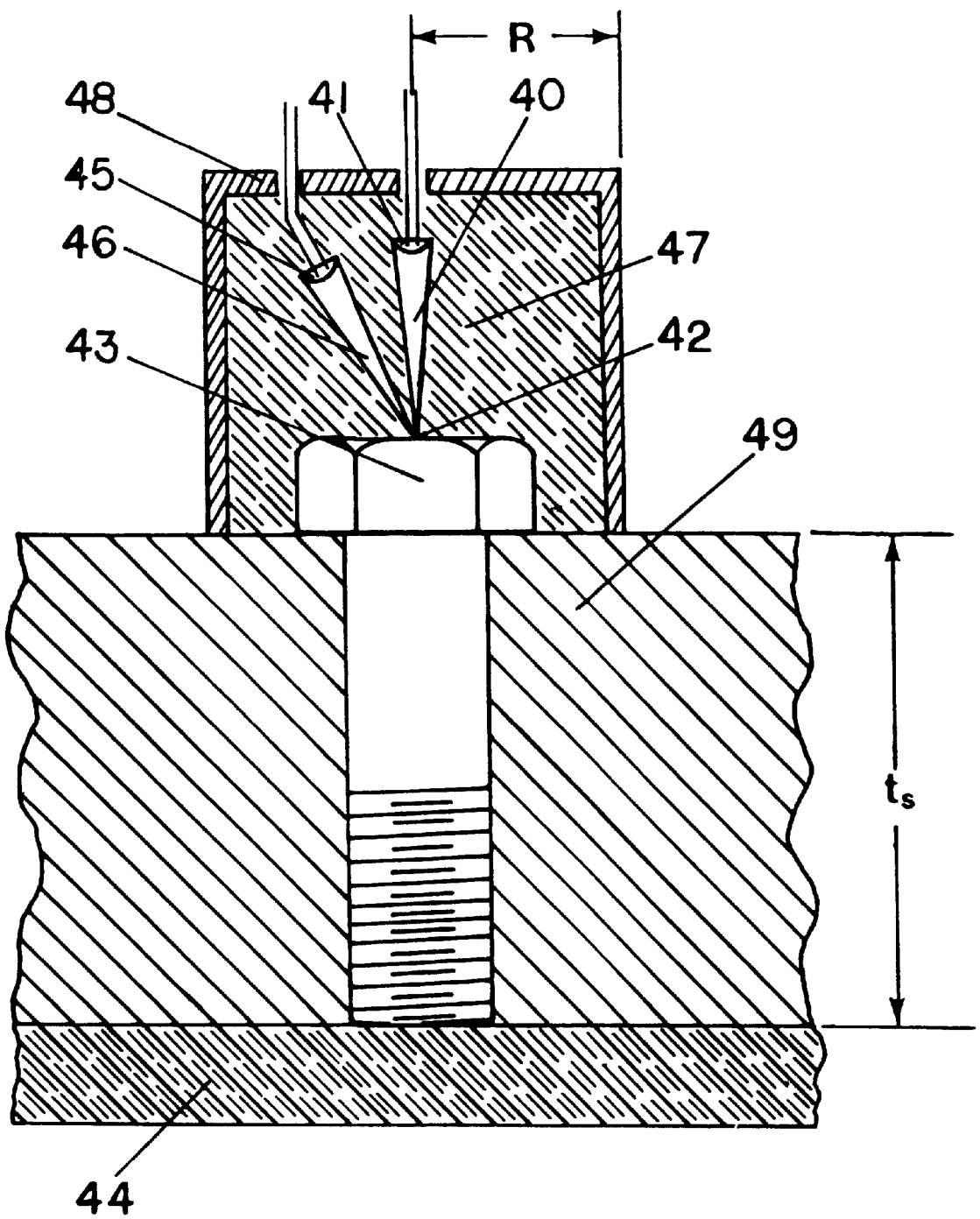
FIG. 4 shows a fastener within a machine assembly sitting on an insulated bed and portions of the apparatus being partly cut away, with a noncontacting laser or infrared heating device and a noncontacting temperature sensor both insulated from each other and surrounded by a cover.

A fourth embodiment is the in situ testing of the fastener: If a fastener of unknown material content is part of an assembly where it is embedded in the component, except for the exposed bolt head, see the schematic representation shown by FIG. 4, then the assembly can be considered thermodynamically as approaching a slab, refer to "The Temperature History and Rate of Heat loss of an Electrically Heated Slab" by A. B. Newman and L. Green, in Transactions of the Electrochemical Society, Vol. LXVI, 1934. According to these authors, if the four edges are heat insulated, or these dimensions are so large compared with the thickness then heat flow toward the edges may be neglected. Through the use of a portable assembly a heat pulse programmed and the instrumentation as described for FIG. 1 can be employed. Simultaneously, with or at a predetermined time after the heat is applied and for a predetermined time interval, or after the heal: has been shut off and for a predetermined time interval, the temperatures or time-varying temperature patterns of the sample, and the standard are sensed or noted and compared. The portable assembly, which can be easily designed to encompass the bolt head 43, includes a laser or infrared heater 40 focused by a lens 41 and the temperature sensed via a focused infrared sensor 46 with focal lens 45, all located at the bolt head 43, which is surrounded by insulation 47 and a cover 48. The infrared sensor 46 is focused via lens 45 within a distance of three or four diameters in relation to the center of the diameter of the small area provided by the infrared heater 40 and focal lens 41. The insulation 47 and the cover 48, shown in FIG. 4, extend a large radial distance R from the center of the bolt, such that the practical case approaches the mathematical case of a thermally insulated slab. Note that the bottom of the assembly is insulated by insulation 44. The radial distance beyond the center of the bolt head that is shown in FIG. 4 should be greater than three or four times the thickness $t_{ss}$ of the slab. The timer 26, energy source 25, for the heating element and the electric switch 24 are as described and programmed as indicated in the embodiment describing FIG. 1. Similarly, the electric power supply 27 for the temperature sensor 46 and the difference amplifier 20 are as described and programmed as indicated in the embodiment describing FIG. 1. The standard, as previously mentioned, is represented by stored data that is the basis of comparison and allows a simple system that is free of comparison samples. As in the embodiment describing FIG. 1, equation (1A) is appropriate and as before stated, it is not necessary that the standard be present. However, since the heater can be focused to a fine spot 42 and the fastener within the component assembly 49 is enclosed and its head 43 insulated, equation (1A) is applicable, as well as the slope equations, equation (2A).

It is noted that for convenience the insulation 47 and the cover 48, shown in FIG. 4 can be removed, (fifth embodiment) and even though the system will lose efficiency due to some heat loss equations (1A) and (2A) are still applicable.

Appropriate instrumentation associated with the application of the subsequent descriptions of the embodiments that follow can readily be employed and is not delineated because it is not necessary to the understanding of the concepts.

If in the system shown in FIG. 4 the heat is turned off, a sixth embodiment, the decay and shape of the temperature-time curve, can be obtained for what is considered here as a bar (a bolt) insulated at its ends, or a slab whose surfaces at x=L and x=0 are insulated. The formulation is given by Carslaw and Jaeger (supra) on page 85, paragraph 36, have provided the governing equation for the temperature distribution through the fastener or slab as:

$$T = 1/L \int_0^L f(x)dx + \qquad (4)$$

$$2/L \sum_{m=1}^{\infty} \exp(-\alpha m^2 \pi^2 t/L^2) \cos(m\pi x/L) \int_0^L f(x)\cos(m\pi x/L)dx$$

Where f(x) is the temperature distribution at the time of shut-off and all other parameters are as previously denoted.

The same input parameters were employed as those outlined in Table 2 and the temperature distributions, f(x) at t=30 seconds, i.e., at shut-off, were obtained for the three bolts insulated at their ends, the grade 8 bolt with the maximum percent chemical variation and the grades 8.2 bolt and grade 8 bolt having minimum percent chemical variation. These functions were then integrated according to equation (4) above to determine the temperature as a function of time at the heated end, i.e., at x=L and their differences were compared. The results showed a positive and negative difference, respectively, between the standard SAE grade 8 bolt of maximum percent chemical variation and the grade 8.2 bolt and grade 8 bolt of minimum percent chemical variation.

The slope and shape of the decay curve, the seventh embodiment, can readily be obtained by differentiating equation (4). This result is given in the following:

$$dT/dt = -2/L \sum_{m=1}^{\infty} (\alpha m^2 \pi^2/L^2) \qquad (5)$$

$$\exp(-\alpha m^2 \pi^2 t/L^2)\cos(m\pi x/L) \int_0^L f(x)\cos(m\pi x/L)dx$$

Again, the same input parameters were employed as those outlined in Table 2 and the slopes and shapes of the decay curves for the cases outlined above were determined according to equation (5). The differences between the slopes of the grade 8 bolt of maximum percent chemical variation and that of the grade 8.2 and grade 8 bolt of minimum percent chemical variation as a function of time were determined to be positive and negative, respectively, at the heat ed end.

Figure 5:
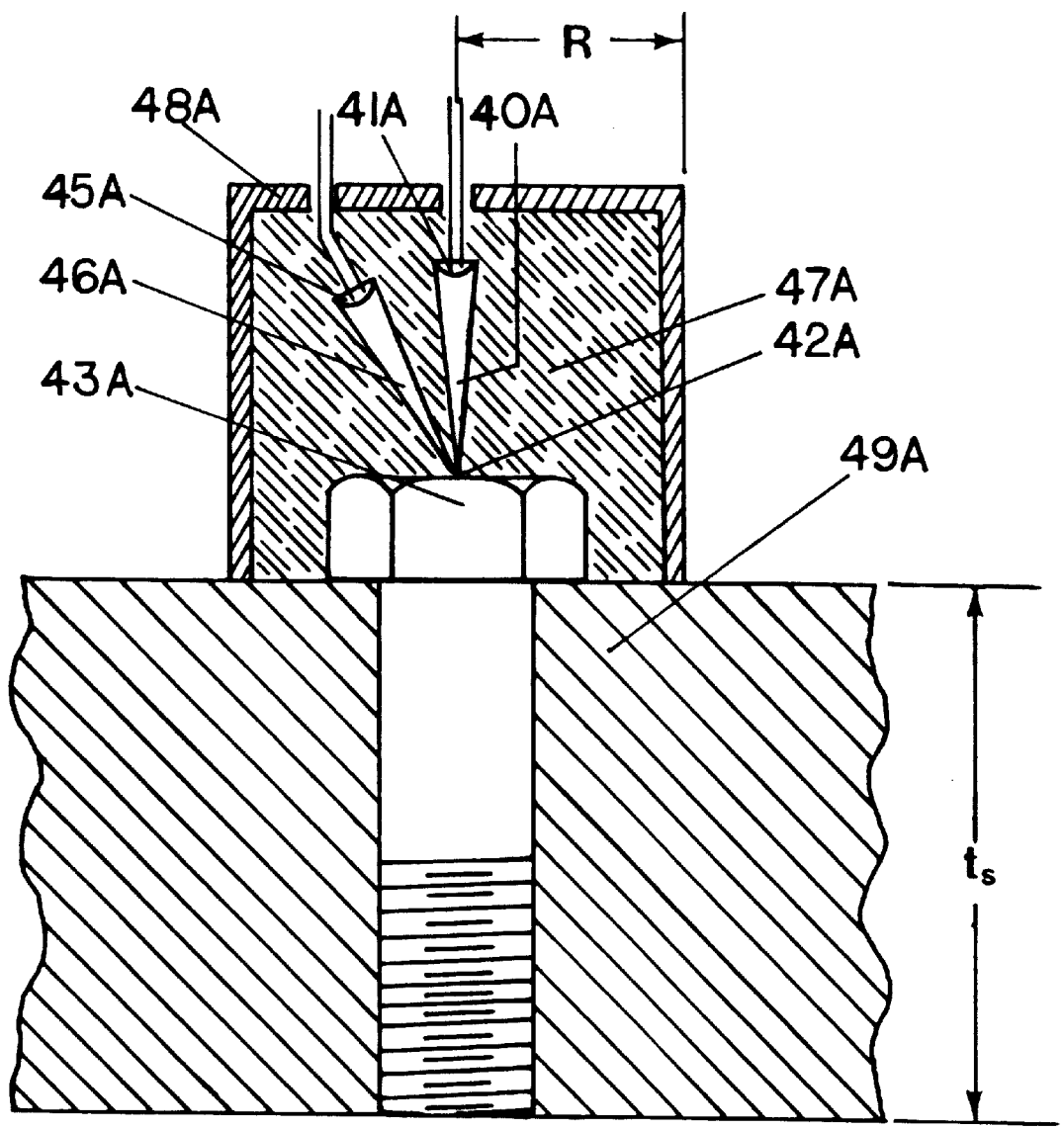
FIG. 5 shows a through-bolt whose end is exposed to the environment within a machine assembly and portions of the apparatus being partly cut away, with a noncontacting laser or infrared heating device and a noncontacting temperature sensor both insulated from each other and surrounded by a cover.

The eighth embodiment is described in the following: The bolt 43A in the assembly 49A, as shown in FIG. 5, is depicted as a through-bolt whose end is exposed to a fluid medium, i.e., oil, water, or air, etc. Again as in previously described embodiments, the heat is applied with or at a predetermined time and for a predetermined time interval, or after the heat has been shut off, the temperatures or time-varying temperature patterns of the sample, and the standard are sensed or noted and compared. This is clearly shown in FIG. 5 where a noncontacting laser or infrared heater 40A of known focal area applies a pulse of heat focused by lens 41A onto a spot on the sample 42A at the bolt head at end 43A and detects this pulse at the same location where detector 46A is focused by focal lens 45A. The detector 46A focused by the lens 45A senses the temperature at a distance within three or four diameters away from the center of the diameter of the heated spot provided by the heater 40A and focused by lens 41A. The standard in this version is represented by stored data that is the basis of comparison and allows a simple system that is free of comparison samples. The electrical signals are processed as previously described in the first embodiment.

It is noted that for convenience the insulation 47A and the cover 48A, shown in FIG. 5 can be removed, however the system will lose some efficiency due to some heat loss.

For these situations Carslaw and Jaeger (supra) on page 104, paragraph 43, have provided a governing equation for the temperature through the fastener as:

$$T(x,t) = Q/k \Big\{ 1/h + x - \qquad (6)$$

$$2 \sum_{m=1}^{\infty} \exp(-\alpha \beta_n^2 t) \cos[(L-x)\beta_n](\beta_n^2 + h^2)/(\beta_n^2[h + L(\beta_n^2 + h^2)]) \Big\}$$

Where all previous parameters are as defined and h=H(T)/k and where H(T) is the coefficient of heat transfer as a function of temperature in BTU/sec-ft²-degree F. where $\beta_n$, n=1,2,3, . . . are the positive roots of the transcendental equation $\beta \tan \beta L = h$.

If the temperature is measured at the heated end and the far end at x=L and x=0 respectively, equation (6) becomes:

$$T = \qquad (6A)$$

$$Q/k \Big\{ 1/h + L - 2\sum_{m=1}^{\infty} \exp(-\alpha \beta_n^2 t)(\beta_n^2 + h^2)/(\beta_n^2[h + L(\beta_n^2 + h^2)]) \Big\}$$

and $$T = Q/k \Big\{ 1/h + \qquad (6B)$$

$$2\sum_{m=1}^{\infty} \exp(-\alpha \beta_n^2 t)\cos[L\beta_n](\beta_n^2 + h^2)/(\beta_n^2[h + L(\beta_n^2 + h^2)]) \Big\}$$

A simplified equation for the coefficient of heat transfer h for a vertical plane surface in laminar air which is a function of temperature was obtained from J. P. Holman, "*Heat Transfer*", McGraw-Hill 1983, page 285. This formula, given by the following, can be appropriately substituted into equation (6A) and (6B) above:

$$h = C(\Delta T/d)^{1/4} \qquad (7)$$

$$h = C(\Delta T/\lambda)^{1/4}$$

Where C is a constant dependent on the body shape, heating or cooling and its orientation, see Table 3 below (from Holman, supra, Table 7.2), ΔT is the difference in temperature between the body and environment and, λ is length of the vertical plane and d is the diameter of the horizontal cylinder.

Equations (6A) and (6B) with equation (7) were used to determine the temperature differences both at the heated and far ends of the fasteners as a function of time. An iteration process was employed in a computer program that included the parameter h as a function of the temperature difference ΔT in equation (7) and the constant C used was 1.32 from Table 3, that of a horizontal cylinder, i.,e., the bolt, whose end is exposed to laminar air. Temperature differences were compared between the grade 8 bolt with the maximum permissible chemical content and the Grade 8.2 bolt and the Grade 8 bolt, both with the minimum permissible chemical content; with the temperature measured at the far end and at the heated end of the fasteners. The same input parameters were employed as those outlined in Table 2. As can be seen from Table 4 below, the results were similar to those presented in Table 2 except that the temperature magnitudes of the fasteners were lower, as expected, and the negative differences, as indicated in Table 4 were somewhat greater.

TABLE 3

CONSTANT C FOR LAMINAR FLOW

| Surface | C |
|---|---|
| Vertical plane or surface | 1.42 |
| Horizontal cylinder | 1.32 |
| Horizontal plate: | |
| Heated plate facing upward or cooled plate facing downward | 1.32 |
| Heated plate facing downward or cooled plate facing upward | 0.61 |

TABLE 4

TEMPERATURE DIFFERENCES BETWEEN STANDARD SAE J 429 AUG83 GRADE 8, MAXIMUM PERCENT CHEMICAL VARIATION CONTENT COMPARED TO MINIMUM PERCENT CHEMICAL VARIATION CONTENT FOR GRADES 8.2 AND GRADE 8 BOLTS; DIAMETER 1 INCH AND LENGTH 1 FOOT, MEASURED AT THE FAR END AND THE HEATED END. ENDS EXPOSED TO AIR Heat input in chart is 500 BTU/hr Temperature Difference in Degrees F.

| | Measured at far end | | Measured at heated end | |
|---|---|---|---|---|
| Time | % Minimum Permissible Chemical Variation | | | |
| sec | 8.2 bolt | 8 bolt | 8.2 bolt | 8 bolt |
| 0 | 0 | 0 | 0 | 0 |
| 5 | 0 | 0 | 0.04 | −0.07 |
| 10 | 0 | 0 | 0.06 | −0.11 |
| 15 | 0 | 0 | 0.07 | −0.14 |
| 20 | 0 | 0 | 0.08 | −0.16 |
| 25 | 0 | 0 | 0.10 | −0.19 |
| 30 | 0 | 0 | 0.11 | −0.20 |

The ninth embodiment, the decay curve for the case indicated above, i.e., the bolt in the assembly shown in FIG. 5, is a through-bolt whose ends are exposed to a fluid medium, i.e., oil, water, or air, etc., can be obtained from Carslaw and Jaeger (supra) on page 97, paragraph 39. These authors have provided a governing equation for the temperature through the fastener as:

$$T = 2\sum_{n=1}^{\infty} \exp(-\alpha\beta_n^2 t)[(\beta_n\cos(\beta_n x) + h\sin(\beta_n x))/(2h + L(\beta_n^2 + h^2))] \times \qquad (8)$$

$$\int_0^L f(x)(\beta_n\cos(\beta_n x) + h\sin(\beta_n x))\,dx$$

Where $\beta_n$, n=1,2,3, ... are positive roots of the transcendental equation: $\tan(\beta L) = 2\alpha h/(\alpha^2 - h^2)$.

The slope and shape for the above case, the ninth embodiment, can be determined by taking the first derivative of equation (8), which is:

$$dT/dt = -2\sum_{n=1}^{\infty} \alpha\beta_n^2 \exp(-\alpha\beta_n^2 t)[(\beta_n\cos(\beta_n x) + \qquad (9)$$

$$h\sin(\beta_n x))/(2h + L(\beta_n^2 + h^2))] \times \int_0^L f(x)(\beta_n\cos(\beta_n x) + h\sin(\beta_n x))\,dx$$

Where the parameters have been previously defined.

Appropriate instrumentation can be readily employed for both the decay curve defined by equation (8) and the slope curve defined by equation (9). Again however, such a description is not considered necessary to the understanding of the concept and thus is not included here.

Figure 6:
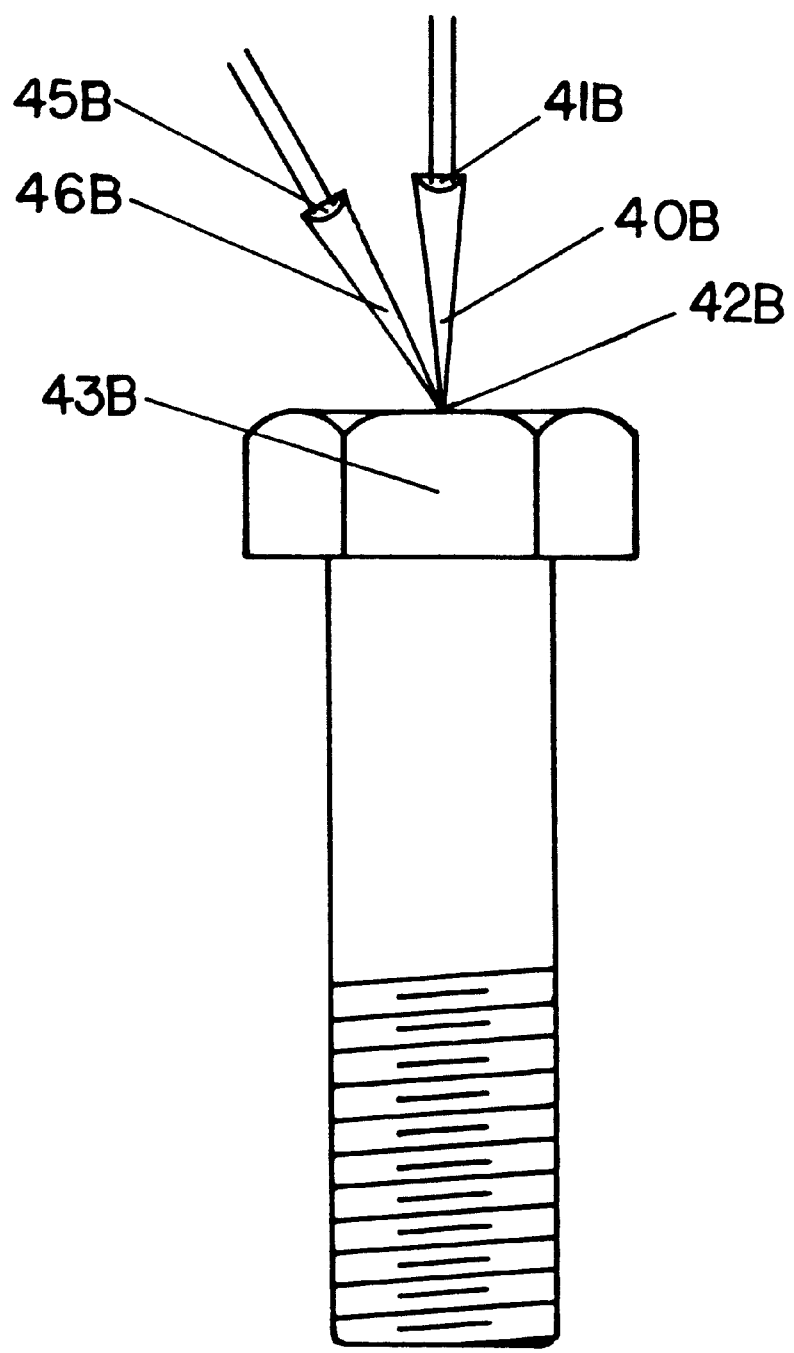
FIG. 6 schematically shows a free standing fastener with a noncontacting laser or infrared heating device and a noncontacting temperature sensor, both located at the head end.

If the mass of the fastener is relatively large compared to the pulse spot, then the tenth embodiment, shown by the test system in FIG. 6, is applicable and the need for housing and insulation is unnecessary. Simultaneously, with or at a predetermined time after the heat is applied and for a predetermined time interval, or after the heat has been shut off and for a predetermined time interval the temperatures or time-varying temperature patterns of the sample, and the standard are sensed or noted and compared. This is clearly shown in FIG. 6 where a noncontacting laser or infrared heater 40B of known focal area applies a pulse of heat focused by lens 41B onto a spot on the sample 42B at the bolt head at end 43B and detects this pulse at the same location where detector 46B is focused by focal lens 45B. The detector 46B focused by the lens 45B senses the temperature within a distance of three to four diameters in relation to the size of the heated area provided by the heater 40B and focal lens 41B. The standard in this version is represented by stored data that is the basis of comparison and allows a simple system that is free of comparison samples. The electrical signals are processed as previously described in the first embodiment.

Figure 7:
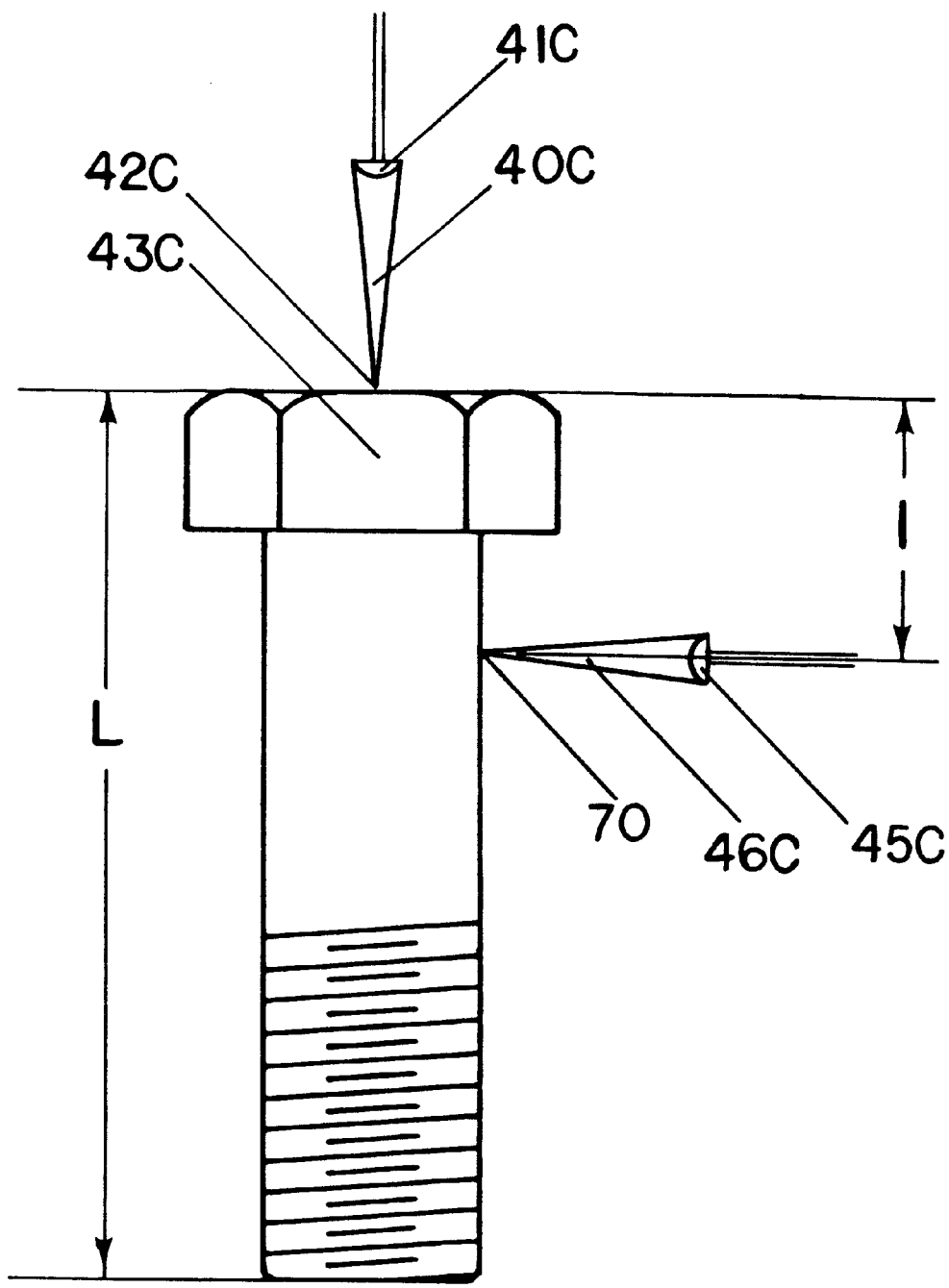
FIG. 7 schematically shows a free standing fastener with a noncontacting laser or infrared heating device located at the head end and a noncontacting temperature sensor located a distance I from the head end.

FIG. 7 shows the eleventh preferred embodiment of this invention. In this unit, an infrared heat source shown 40C is focused by a lens 41C on the head 42C of a large bolt 43C. Simultaneously, with or at a predetermined time after the heat is applied and for a predetermined time interval, or after the heat has been shut off and for a predetermined time interval the temperatures or time-varying temperature patterns of the sample, and the standard are sensed or noted and compared. The spot size is approximately ¹⁄₁₀th of the diameter of the bolt and ideally ¹⁄₂₀th of this diameter for sizes over ½ inch diameter. The pulse from this infrared heater is focused on the bolt head for a set timed interval of 30 seconds or less as long as a signal is transmitted to the bolt. The infrared temperature sensor shown as 46C is focused by a focal lens 45C on a spot 70 on the shank of the fastener which is I distance away from the input pulse of heat. The length I is ⅒ of the bolt length, 1.2 inches in this case where the bolt is 12 inches long and 1 inch in diameter.

Alternatively, an electromagnetic heater, the twelfth preferred embodiment, such as that described in U.S. Pat. No. 4,385,843 can be used as a heat source in place of 40C and 41C shown in FIG. 7.

The heat pulse is applied or terminated and the infrared temperature sensor is focused on the spot at distance I, see FIG. 7. This sensor will show a temperature change with time as the perturbation of the temperature travels down the bolt through heat transmission. The heat pulse is also diminished with time as it spreads and the bolt acts as a heat sink. This is not as perfect a heat sink as the precious metals that have been tested end to end; the end pulse in a bolt would not be a good test signal. In an alloyed steel or a carbon steel the signal taken near the input point is, however, strongly affected by the alloying elements, or lack thereof; in non-precious metals the pulse dissipates in different ways as the alloying elements change in content.

The pulse generated is measured and then compared to the data bank of other reference information. The information can even be manually sorted and discriminated. In very large bolts the size effect is minimal, for smaller bolts comparative data is needed. However, means for accommodating several sizes and utilizing the same computer for all sizes can readily be accomplished with simple portable computers.

Figure 8:
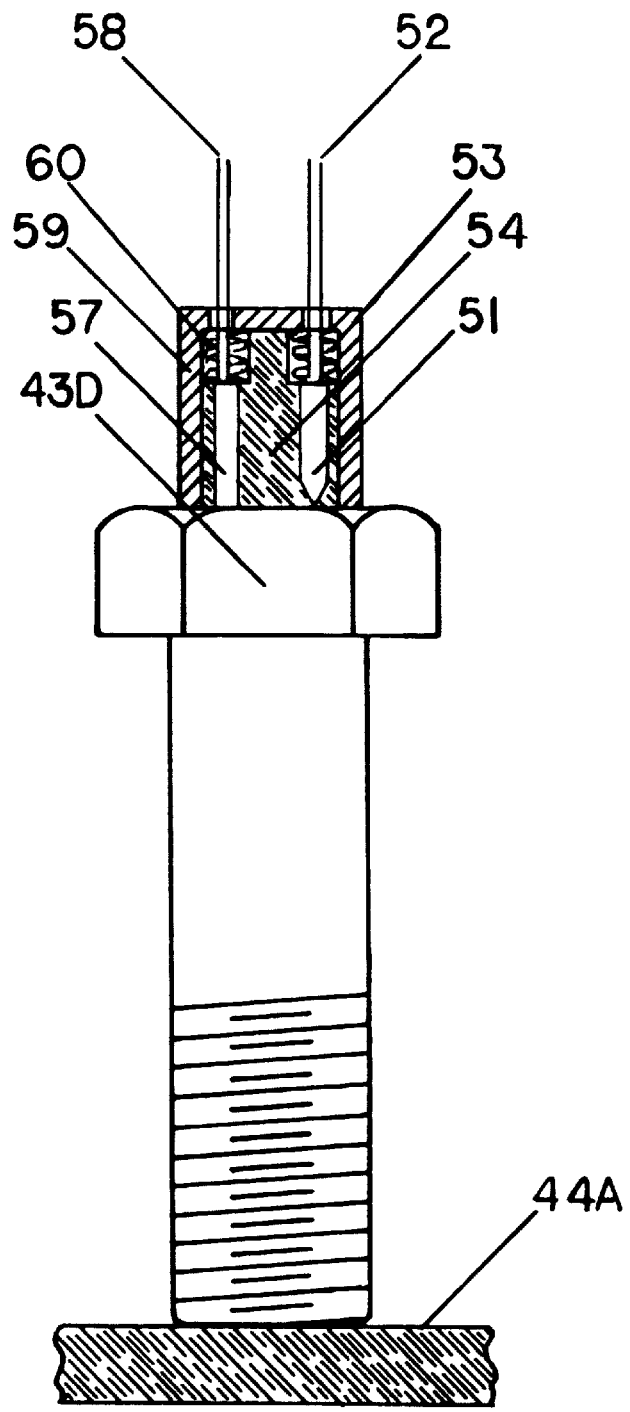
FIG. 8 is a schematic of a portable heater and sensor in contact with the subject fastener at the head end; and portions of the apparatus being partly cut away.

In FIG. 8, a dual contacting probe, is the thirteenth embodiment shown where the heater 57 is a contact heater, energized by an electrical pulse through lead wires 58, and the temperature sensor 51 is a contact sensor, where its signal is transmitted by lead wires 52. The assembly is mounted in a handy and compact housing 59 that is well insulated 54 and the components are insulated one from the other. The temperature sensor must be of small mass due to the nature of the input signal. A thin film detector, such as a foil grid thermocouple, can be used to insure sensitivity. In this case the probe is in a common housing 59 and the temperature sensor and heater are forced against the head 43D of the fastener by springs 53 and 60, respectively. The assembly is supported on an insulated base 44A or any mechanical spring gripping mechanism that forces the housing 59 against the head of the bolt. This is not shown because it is not necessary to the understanding of the basic concept. The test could also be made on the shank or any other point subject to getting good contact.

Figure 9:
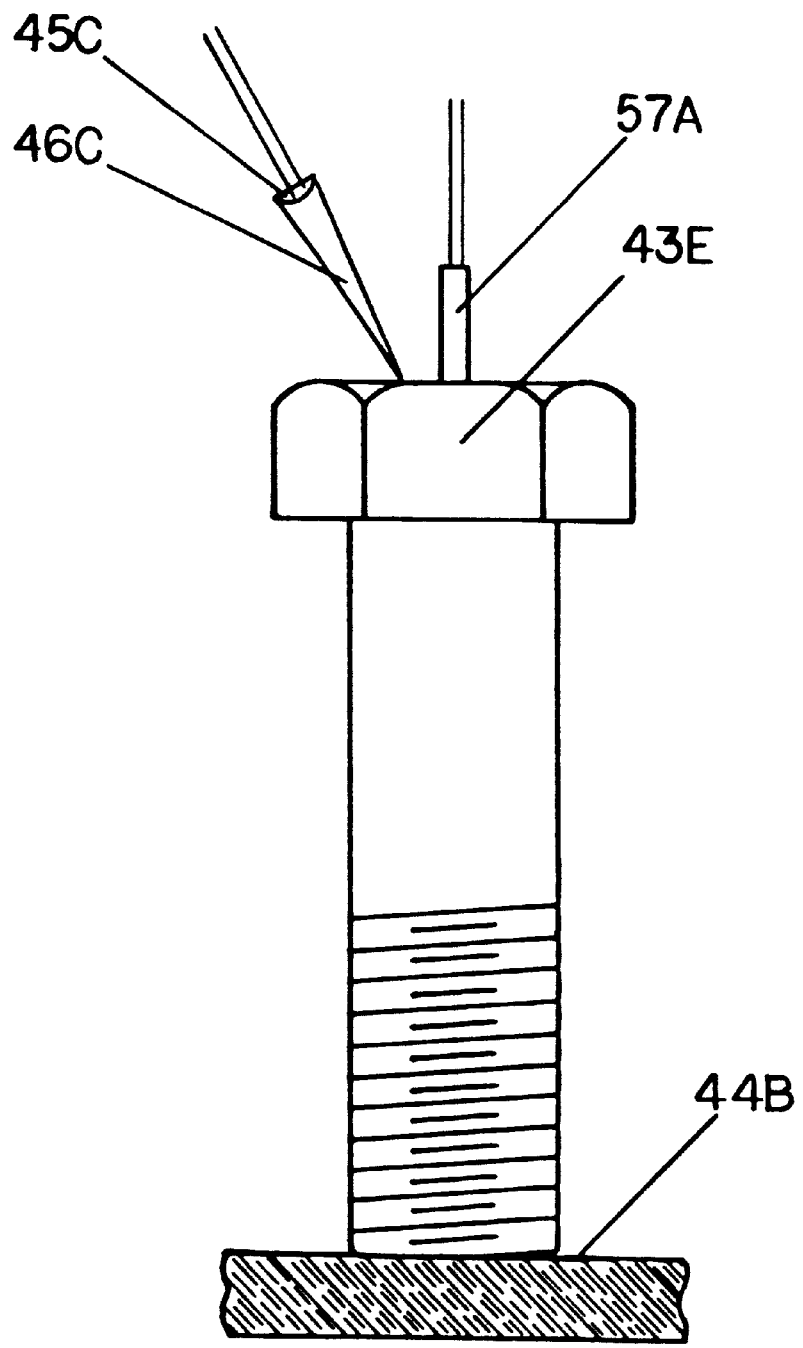
FIG. 9, is another schematic, shows a mixed system with a heater in contact with the subject fastener and a noncontacting infrared sensor focused on a spot at the heat input end of the fastener.

In FIG. 9, a hybrid system, shows the fourteenth embodiment to the invention. The mixing of the infrared temperature sensor 46C with its focussing lens 45C and the contact heater 57A with its spring (not shown) forcing the heater against the bolt head 43E, or other combination is to be expected in various forms of this invention. The assembly is supported on an insulated base 44B or any mechanical spring gripping mechanism can be utilized that forces the heater 57A and the sensor 46C against the head of the bolt. This is not shown because it is not necessary to the understanding of the basic concept.

Notice that the temperature differences shown in Table 2, which is in the background section, are all based on heat input. In this, the fifteenth embodiment, the input is a cold pulse and the cold pulse can be created, for example, by evaporation of a known amount of liquid nitrogen restrained in a tube and employed as the thermal pulse with an accompanying temperature drop. Here the result is also great enough to be readily measured even for the large fastener size chosen as an example and avoids the use of heat.

The apparatus herein described provides fast, foolproof and economical determination of composition, and thermal properties of samples in a system which avoids the high skill needed for such determination by observing surface temperatures. The device will discriminate between the standard Society of Automotive Engineers designated standard grade 8 fastener and the grade 8.2 fastener and most of those used as counterfeits. In addition, it will distinguish between the grade 8 standard fastener, as well as the steel alloys accepted as substitutes for the grade 8 standard, and many of those carbon steel fasteners that are used as counterfeits and thus serve as a screening device. Those minimal number of tested samples that remain questionable regarding their authenticity can then be tested by one of the definitive or comparative methods of determining the composition of metallic materials mentioned previously in the "Prior Art" section.

The device makes possible such analyses enclosed herein by unskilled persons and in the case of many materials, particularly ferrous fasteners, it makes possible improved testing and checking of samples, compared to U.S. Pat. Nos. 3,981,175 and 4,381,154 for which no such procedure was presented, and if it had it would not be successful. Several improvements over U.S. Pat. No. 5,052,819, already stated, have been realized. The accuracy of results is related to the size of the fastener and the prescribed time interval of testing, as well as the quality of electronics employed.

Further modification of these improvements over the original invention herein disclosed, will occur to persons skilled in the art and all such modifications are deemed to be within the spirit and scope of this invention as defined by the appended claims.

I claim:

1. A system for discriminating between an alloy content in a sample and materials having known alloy contents comprising:

thermal pulse means for applying a thermal pulse to a focused spot on said sample, wherein said focused spot has a diameter which is approximately ½₀th the diameter of the sample, thus converting the sample into a thermally equivalent slab of metal, a sensor positioned between three and four spot diameters from the focused spot, as measured from the center of the focused spot for measuring transmission of said pulse through said sample and generating a signal representative thereof, and means for comparing said signal to transmission properties of materials having known material alloy contents to discriminate the sample therefrom.

2. The system of claim 1 wherein said thermal pulse means is a focused infrared beam generator.

3. The system of claim 1 wherein said thermal pulse means is a focused laser radiation generator.

4. The system of claim 3 wherein the sensor is positioned at the focal point of the focused spot.

5. The system of claim 1 wherein said thermal pulse is a positive thermal pulse.

6. The system of claim 1 wherein said thermal pulse is a negative thermal pulse.

7. The system of claim 1 wherein said thermal pulse means is a contact heater.

8. The system of claim 1 wherein said sensor is a lightweight thermocouple or thermopile sensor.

9. The system of claim 1 wherein said sensor is an infrared thermal detector.

10. The system of claim 1 further comprising a reference data library for storing the transmission properties of materials having known material alloy contents.

11. The system of claim 1 wherein the transmission properties of materials having known material alloy contents are simultaneously measured from known samples.

12. A method for detecting alloy content in a sample including the steps of:

applying a thermal pulse for a predetermined length of time to a focused spot on said sample, wherein said focused spot has a diameter which is approximately 1/20th the diameter of the sample, thus converting the sample into a thermally equivalent slab of metal, positioning a sensor at a location between three and four spot diameters from the focused spot, as measured from the center of the focused spot, measuring a shape and slope of a thermal decay curve of the sample with the sensor upon discontinuation of the thermal pulse, generating a signal with said sensor represenative of the shape and slope of the thermal decay curve of the sample, and comparing said signal to predetermined properties of materials having known material allow contents and discriminating the sample therefrom, to thereby screen the sample for alloy content.

13. The method of claim 12 wherein said step of applying a thermal pulse further comprises generating a focused infrared beam.

14. The method of claim 12 wherein said step of applying a thermal pulse further comprises generating a focused laser beam.

15. The method of claim 12 wherein the positioning step further comprises positioning the sensor at the focal point of the focused spot.

16. The system of claim 12 wherein said step of applying a thermal pulse further comprises applying a positive thermal pulse.

17. The system of claim 12 wherein said step of applying a thermal pulse further comprises applying a negative thermal pulse.

18. The method of claim 12 further comprising the steps of:

storing transmission properties of materials having known material alloy contents in a reference data library; and comparing said signal to the properties stored in said reference data library and discriminating the sample therefrom, to thereby screen the sample for alloy content.

19. The method of claim 12 further comprising the steps of:

simultaneously measuring the thermal transmission properties of materials having known alloy contents; and comparing said signal to the simultaneously measured properties and discriminating the sample therefrom, to thereby screen the sample for alloy content.

* * * * *